United States Patent [19]

Sheridan et al.

[11] Patent Number: 4,834,723
[45] Date of Patent: May 30, 1989

[54] THORACIC CATHETERS

[75] Inventors: David S. Sheridan, Argyle; Isaac S. Jackson, Greenwich, both of N.Y.

[73] Assignee: Sheridan Catheter Corp., Argyle, N.Y.

[21] Appl. No.: 842,714

[22] Filed: Mar. 19, 1986

Related U.S. Application Data

[63] Continuation of Ser. No. 631,459, Jul. 16, 1984, abandoned.

[51] Int. Cl.$^4$ .............................................. A61M 5/32
[52] U.S. Cl. ..................................... 604/274; 604/280
[58] Field of Search ............... 604/263, 280, 274, 174, 604/170

[56] References Cited

U.S. PATENT DOCUMENTS

| 3,190,290 | 6/1965 | Alley et al. | 604/200 |
| 3,508,554 | 4/1970 | Sheridan | 604/280 |
| 3,589,368 | 6/1971 | Jackson et al. | 604/280 |
| 3,605,725 | 9/1971 | Benton | 604/280 |

Primary Examiner—John D. Yasko
Attorney, Agent, or Firm—Burns, Doane, Swecker & Mathis

[57] ABSTRACT

Thoracic catheters to be implanted in the chest or other body portion of a patient by withdrawal of the proximal end through a secondary incision at a suitable site are improved by having a tapered proximal end portion thereon which has a smoothly contoured nose through which a small lumen extends that permits the surgeon to securely grasp the catheter with a Kelly clamp by having one jaw of the clamp inside the nose lumen and the other jaw on the outside of the nose.

5 Claims, 2 Drawing Sheets

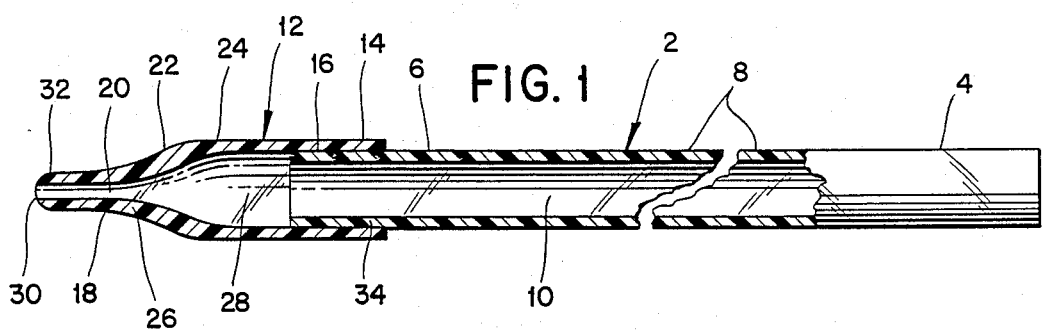
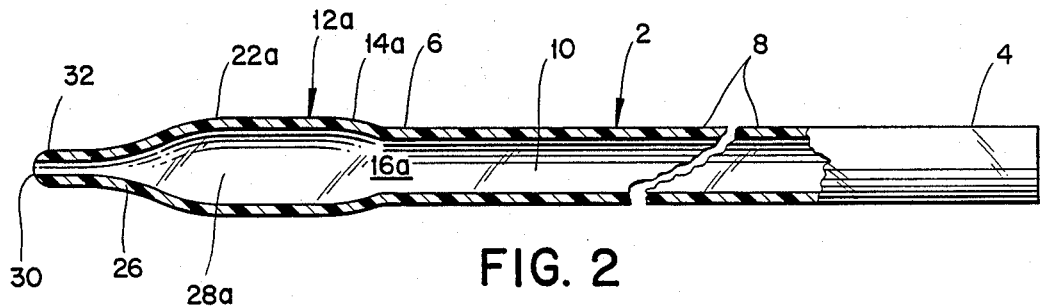
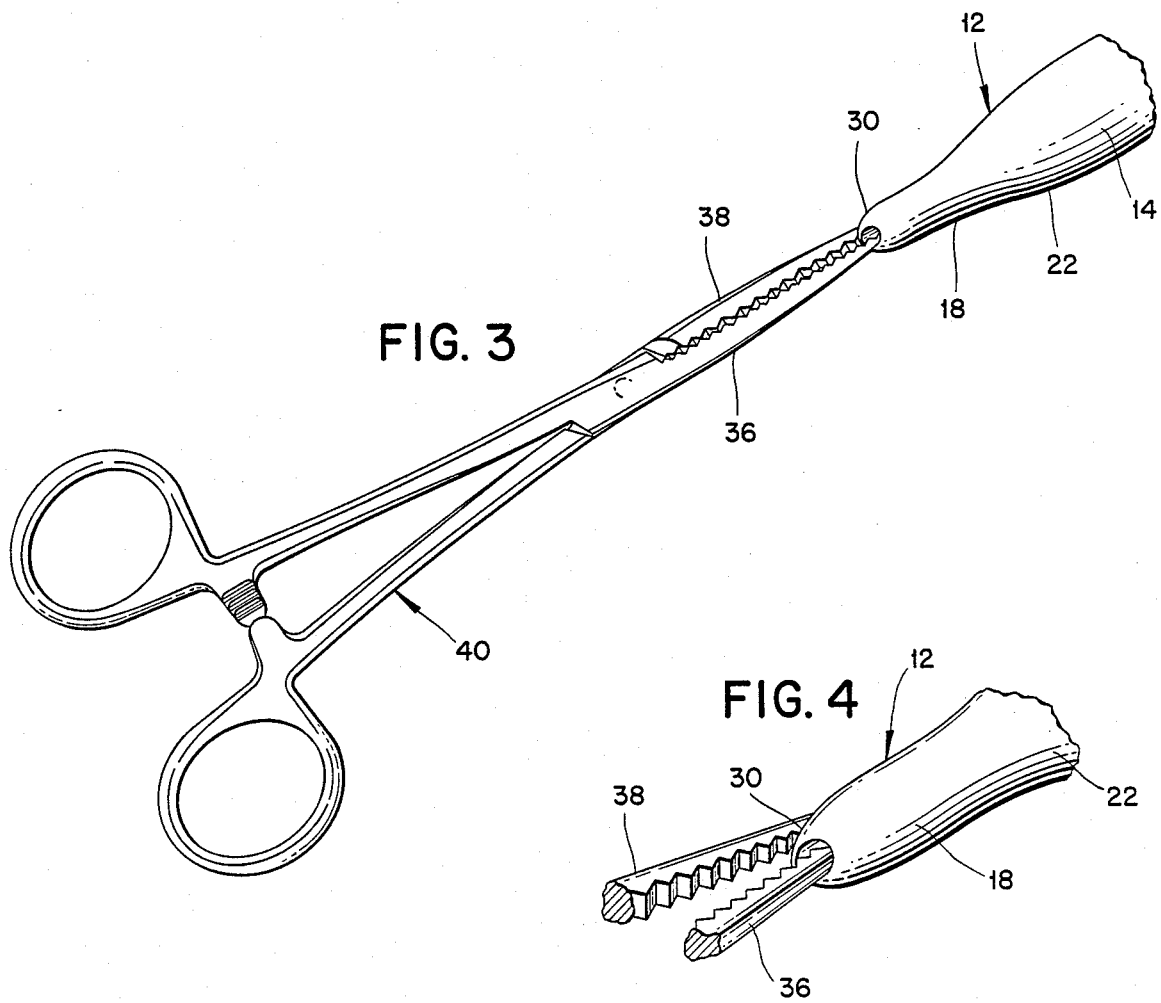

THORACIC CATHETERS

This application is a continuation of Ser. No. 631,459 filed July 16, 1984, now abandoned.

BACKGROUND OF THE INVENTION

1. Field of the Invention

This invention relates broadly to medico-surgical tube devices (MSTD). More particularly, it concerns thoracic catheters, i.e., MSTD that are designed for postsurgical drainage purposes to remove fluids or other matter from the chest or other body cavities of patients.

2. Description of the Prior Art

Thoracic catheters are also variously referred to by surgeons and other persons that work with them as postsurgical drainage tubes and intercostal catheters. By whatever name they may be called, this class of MSTD are positioned in a patient at the completion of a surgical procedure to remove body fluids that are invariably generated by the patient's body as a consequence of the surgery. This invention may be utilized generally with this class of MSTD.

The use of the primary incision created by the surgical procedure on the patient as an exit for thoracic catheters is usually avoided to safeguard against contamination of the body cavity from which fluid is to be withdrawn by the catheter. Instead, the surgeon determines a suitable site other than the primary incision and makes a short secondary incision for catheter withdrawal. The proximal end of the catheter is then inserted through the primary incision and threaded toward the secondary incision. The surgeon then inserts an instrument, such as a Kelly clamp, from the outside of the patient into the secondary incision and grasps the proximal end of the catheter with the clamp to draw it through the secondary incision leaving the distal end properly located in the patient's body. Hence, this type of implantation of a catheter is opposite to the more conventional method in which the distal end of a catheter first enters the patient's body.

It has been recognized by catheter designers that the leading proximal end (sometimes called machine end) of thoracic catheters and the procedure needed to effect their implantation should cause minimal damage to tissue at the secondary incision site. One catheter design for this purpose has the proximal end cut with a long taper (see U.S. Pat. Nos. 3,190,290 and 3,295,527). This helps in withdrawing the catheter by permitting firm grasp of the end with a clamp, but the taper cut leaves raw cut edges that can damage tissue.

Another design uses a closed end nose having a nipple-like tip on the proximal end of the thoracic catheters (see U.S. Pat. No. 3,589,368). While this design mitigates tissue damage, the nipple tip is grasped on the outside by the jaws of the Kelly or like clamp. Hence, the overall width of both jaws with the nose tip between them is substantially increased and the grasping of the nose in this design with the clamp is not as positive as in the tapered cut design.

OBJECTS

A principal object of the present invention is the provision of new, improved forms of thoracic catheters. Further objects include the provision of:

1. Improved forms of thoracic catheters that will mitigate trauma to the patient during implantation.

2. Such catheters having a form of proximal end nose that insures positive grasping thereof by a Kelly clamp or like instrument during the implant procedure, while reducing to a minimum the width of separation of the clamp jaws in performing the nose grasping.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by the provision of thoracic catheters made of flexible plastic material having a distal end portion, a proximal end portion, a central body portion connecting the distal end portion to the proximal end portion and a major lumen extending centrally along the length of the catheter characterized by an improved type of proximal end nose.

In a preferred embodiment, an improved proximal end nose of the invention comprises a distal section with a first lumen substantially equal to the lumen of the remainder of the catheter, a proximal tubular section having a second lumen at least several times smaller than the first lumen and a central section with a third lumen substantially larger than the first and second lumens. The central section integrally connects the proximal section to the distal section. There is a smoothly rounded tip on the nose and the second lumen extends through the tip.

In a second embodiment, a proximal end nose of the invention is not formed integral with the remainder of the catheter and comprises a distal tubular section having a first lumen substantially equal to the O.D. of the remainder the catheter and the outside of the proximal end portion of the catheter is cemented or fused into such first lumen.

Advantageously, the new thoracic catheters are made of plasticized polyvinyl chloride and the plastic material of which noses of the second embodiments are made is flexible plasticized polyvinyl chloride.

BRIEF DESCRIPTION OF THE DRAWINGS

A more complete understanding of the invention may be had by reference to the accompanying drawings in which:

FIG. 1 is a lateral, fragmentary view, partially in section, of a thoracic catheter constructed in accordance with the invention.

FIG. 2 is a lateral, fragmentary view, partially in section, of another preferred embodiment of thoracic catheters of the invention.

FIG. 3 is a perspective, fragmentary view of the proximal end of the thoracic catheter of FIG. 1 grasped by a Kelly clamp.

FIG. 4 is an enlarged, fragmentary, perspective view of the tip of a proximal end nose for a thoracic catheter made in accordance with the invention.

DESCRIPTION OF THE PREFERRED EMBODIMENTS

Figure 5:
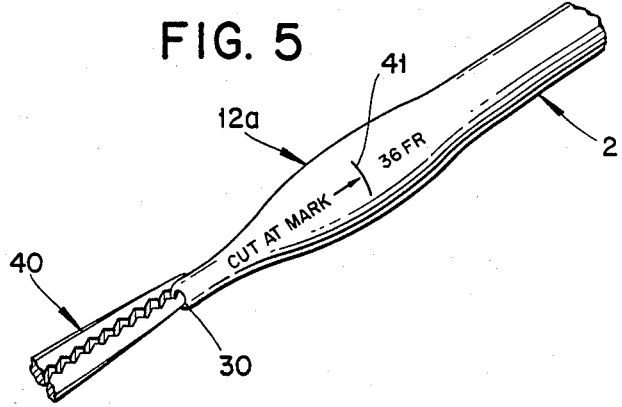
FIG. 5 is a perspective, fragmentary view of the proximal end of the thoracic catheter of FIG. 2.

Referring in detail to the drawings, in the embodiment of FIG. 1, the thoracic catheter 2 made of flexible plastic material has a distal end portion 4, a proximal end portion 6, a central body portion 8 integrally connecting the distal end portion 4 to the proximal end portion 6 and a major lumen 10 extending centrally along the length of the catheter 2.

The improved type of proximal end nose 12 made of plastic material comprises a distal tubular section 14 that has a first lumen 16 substantially equal to the O.D. of the proximal end portion 6 of the catheter 2, a proximal tubular section 18 having a second lumen 20 at least several times smaller than the first lumen 16 and a central section 22 that contracts in diameter proximally from its distal region 24 to the distal region 26 of the proximal tubular section 18. The central section 22 defines a third lumen 28 and integrally connects the proximal tubular section 18 to the distal tubular section 14.

There is a smoothly rounded tip 30 on the proximal end 32 of the nose 12 and the second lumen 18 extends through the tip 30.

The outside of the end 34 of the proximal portion 6 of the catheter 2 is fixed in fluid tight union with the first lumen 16 such as by cementing or fusion of the separate parts.

The new thoracic catheters, advantageously, are made of plasticized polyvinyl chloride and the plastic material of which the noses 12 are made is flexible plasticized polyvinyl chloride. Alternatively, the plastic material of the catheters and new noses may be polyethylene, polypropylene or similar plastics. The catheters 2, per se, are made of flexible plastic while the noses 12 may be made of flexible, semi-rigid or rigid plastic.

The technique used to implant the new thoracic catheters in a patient are illustrated in FIGS. 3 & 4. Thus, the tip 30 of nose 12 is grasped by the jaws 36 & 38 of the Kelly clamp 40. In doing this, the jaw 36 extends into the second lumen 20 while the other jaw 38 bears against the outside of the tip 30. As a result, the jaws 36 & 38 of the clamp 40 are minimally separated while effectively, and very positively, grasping the end nose 12. Also, because of the smoothly contoured shape of the nose 12 including the tip 30, the thoracic catheters 2 of the invention may be drawn through secondary incisions in patients with a absolute minimum of trauma, i.e., there is no tendency for the noses 12 to "core" or otherwise damage tissue during the catheter implantation procedure.

In the preferred embodiment of the invention as shown in FIG. 2, an improved proximal end nose 12a of the invention comprises a distal section 14a with a first lumen 16a substantially equal to the lumen 10 of the remainder of the catheter 2, a proximal tubular section 18a having a second lumen 20 at least several times smaller than the first lumen 16a and a central section 22a with a third lumen 28a substantially larger than the first and second lumens. The central section 22a integrally connects the proximal section 18a to the distal section 14a. There is a smoothly rounded tip 30 on the nose 12a and the second lumen 20 extends through the tip 30.

The improved catheter noses 12 or 12a may comprise a mark 41 to indicate to the surgeon or other user the position to cross cut the nose to remove the proximal section thereof to form a funnel end so the catheter installed in the patient may be connected to suction equipment (not shown).

Figure 6:
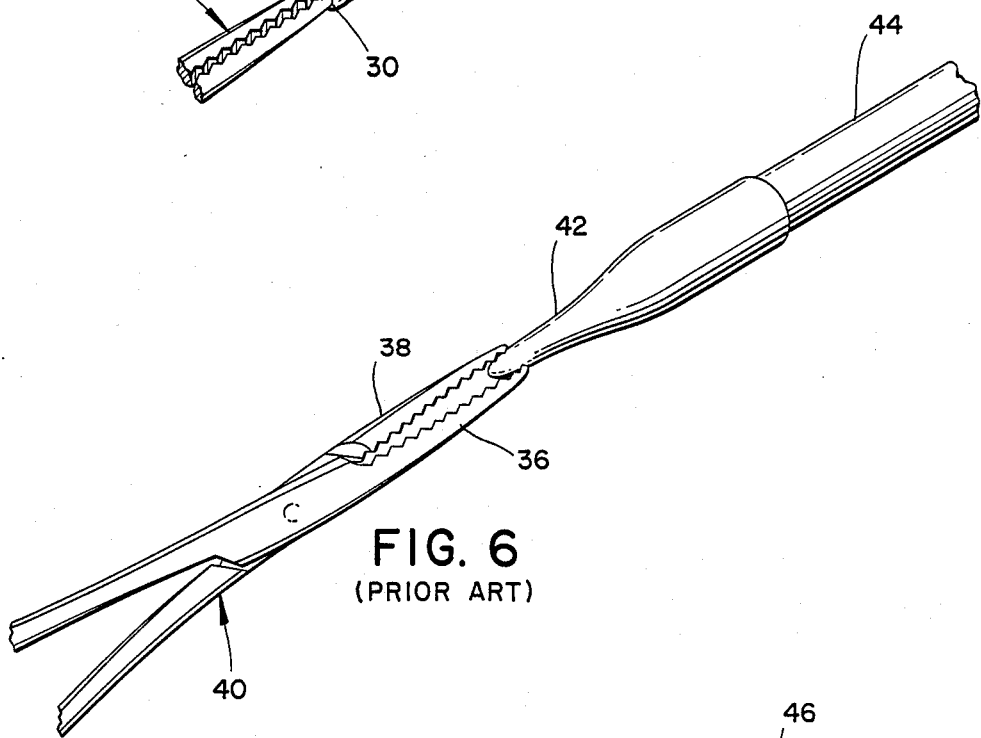
FIG. 6 is a perspective view similar to FIG. 3 showing a form of thoracic catheter of the prior art grasped by a Kelly clamp.

FIG. 6 illustrates the end nose 42 of a thoracic catheter 44 of the prior art as disclosed in U.S. Pat. No. 3,589,368 being grasped by the clamp 40. As can be seen, since the jaws 36 & 38 of the clamp 40 must both bear on the outside of the nose 42, they are substantially more separated form each other than when grasping the end nose 12 of the thoracic catheters of the invention as seen in FIG. 3. Additionally, the grasp of the nose 42 because of the wider separation of the jaws 36 & 38 is not as positively secure as the grasp of the new noses 12 by the clamp 40.

Figure 7:
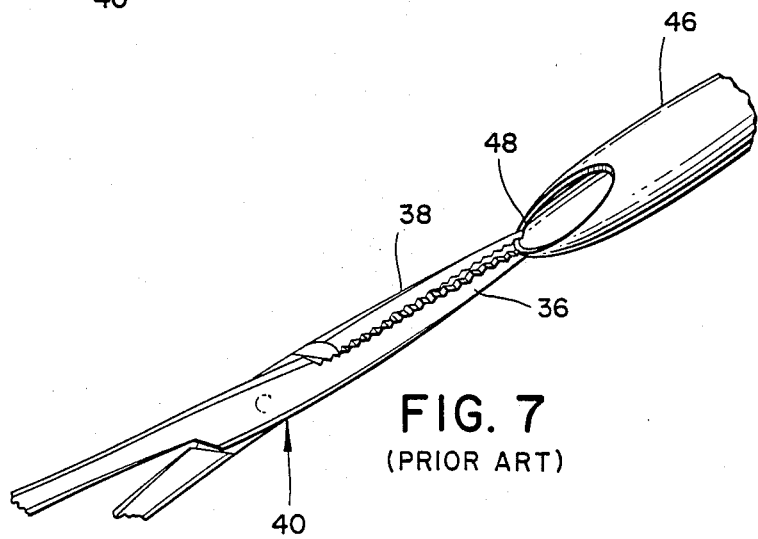
FIG. 7 is a perspective view similar to FIG. 3 showing another form of thoracic catheter of the prior art grasped by a Kelly clamp.

FIG. 7 illustrates the end nose 46 of another prior art thoracic catheter 46 such as disclosed in U.S. Pat. No. 3,190,290 being grasped by the clamp 40. In this case, the separation of the jaws 36 & 38 of the clamp 40 are less then in the case shown in FIG. 4, but because of the width and nature of the taper cut 48 in the thoracic catheter 46, there is substantially greater possibility for the catheter 46 to produce tissue trauma during the implantation of this style thoracic catheter as compared to those of the present invention.

The embodiments of the invention in which an exclusive property or privilege is claimed are defined as follows:

1. In a thoracic catheter made of flexible plastic material having a proximal end portion, a distal end portion, a central body portion integrally connecting said proximal end portion to said distal end portion and a major lumen extending centrally along the length of the catheter, the improvement of an improved proximal end nose made of plastic material which comprises:
   a distal tubular section having a first lumen at least equal to said major lumen of said catheter,
   a proximal tubular section having a second lumen at least several times smaller than said first lumen,
   a central section that contracts in diameter proximally from its distal region to the distal region of said proximal tubular section,
   said central section defining a third lumen and integrally connecting said distal tubular portion to said proximal tubular portion, and
   a smoothly rounded tip on said proximal tubular section, said second lumen extending through said tip.

2. The thoracic catheter of claim 1 wherein said flexible plastic material is plasticized polyvinyl chloride and the plastic material of which said nose is made is flexible plasticized polyvinyl chloride.

3. The thoracic catheter of claim 1 wherein said proximal end nose is separately formed from said catheter, said first lumen is substantially equal to the O.D. of said proximal portion of said catheter and the outside of said proximal end portion of said catheter is fixed in fluid tight union with said first lumen.

4. The thoracic catheter of claim 1 wherein said proximal end nose is formed integrally with the remainder of the catheter and said first lumen and major lumen are substantially identical.

5. In a thoracic catheter made of flexible plastic material having a proximal end portion, a distal end portion, a central body portion integrally connecting said proximal end portion to said distal end portion and a major lumen extending centrally along the length of the catheter, the improvement of an improved proximal end nose made of plastic material which comprises:

a proximal end nose made of plastic material comprising a distal tubular section that has a first lumen substantially equal to the O.D. of said proximal end portion of the catheter, a proximal tubular section having a second lumen appreciably smaller than said first lumen and a central section that contracts in diameter proximally from its distal region to the distal region of said proximal tubular section, said central section defining a third lumen and integrally connecting said proximal tubular section to said distal tubular section and a smoothly rounded tip on said proximal tubular section, said second lumen extending through said tip.

* * * * *